United States Patent [19]

Order

[11] Patent Number: 5,424,288
[45] Date of Patent: Jun. 13, 1995

[54] METHOD OF TREATING SOLID TUMOR CANCERS UTILIZING MACRO AGGREGATED PROTEINS AND COLLOIDAL RADIOACTIVE PHOSPHOROUS

[76] Inventor: Stanley E. Order, 1123 Chanticleer, Cherry Hill, N.J. 08003

[21] Appl. No.: 187,588

[22] Filed: Jan. 26, 1994

Related U.S. Application Data

[63] Continuation-in-part of Ser. No. 183,463, Jan. 19, 1994, which is a continuation-in-part of Ser. No. 945,089, Sep. 15, 1992, abandoned, which is a continuation-in-part of Ser. No. 843,367, Feb. 28, 1992, abandoned.

[51] Int. Cl.$^6$ .............. A61K 38/38; A61K 51/00; C07K 14/76; A61M 36/00
[52] U.S. Cl. .............. 514/2; 424/1.11; 424/1.29; 424/422; 514/965; 530/362; 600/3; 600/4
[58] Field of Search .............. 600/3, 4; 424/422, 1.1, 424/1.11, 1.29; 514/2, 965; 530/362

[56] References Cited

U.S. PATENT DOCUMENTS

Re. 33,375  10/1990  Luck et al. .............. 514/2

OTHER PUBLICATIONS

TechneScan® MAA product literature, Kit for the Preparation of Technetium Tc 99m Albumin Aggregated, sold by Mallinckrodt Medical Inc., St. Louis, Mo, 63134, revised Sep. 1992, 1 page, 2 sides.
MPI MAA Kit brochure, Medi-Physics Inc, 1990.

*Primary Examiner*—David L. Lacey
*Assistant Examiner*—Ron Schwadron
*Attorney, Agent, or Firm*—Caesar, Rivise, Bernstein, Cohen & Pokotilow, Ltd.

[57] ABSTRACT

A method of treating solid tumor cancer in a living being by prolonging the time a therapeutically effective agent remains in the tumor. The method comprises the steps of selecting particles of an aggregated protein and injecting them interstitially into the tumor. The therapeutically effective agent colloidal radioactive phosphorous is injected into the tumor either after the injection of the proteinaceous particles, or simultaneously.

3 Claims, No Drawings

METHOD OF TREATING SOLID TUMOR CANCERS UTILIZING MACRO AGGREGATED PROTEINS AND COLLOIDAL RADIOACTIVE PHOSPHOROUS

RELATED APPLICATIONS

This application is a continuation-in-part of application Ser. No. 08/183,463, filed on Jan. 19, 1994, entitled METHOD AND COMPOSITIONS FOR DELIVERING CYTOTOXIC AGENTS TO CANCER, which was a continuation-in-part of application Ser. No. 07/945,089, filed on Sep. 15, 1992, now abandoned, entitled USE OF AGGREGATED PROTEINS TO PROLONG RETENTION TIME OF A THERAPEUTIC AGENT ADJACENT A TARGETED SITE SUCH AS A TUMOR, which is a continuation-in-part of application Ser. No. 07/843,367, filed on Feb. 28, 1992, now abandoned, entitled USE OF AGGREGATED PROTEINS TO PARTIALLY OR TOTALLY DIMINISH VASCULAR FLOW TO A TUMOR OR TUMOR BEARING REGION, now abandoned, the entire disclosures of which are incorporated by reference herein.

BACKGROUND OF THE INVENTION

Throughout the years, the treatment and/or cure of cancer and other diseases has been intensely investigated culminating in a wide range of therapies. Cancer has typically been treated with surgery, radiation and chemotherapy, alone or with various therapies employing drugs, biologic agents, antibodies, radioactive immunconjugates, lymphocytes, macrophages, etc. (sometimes collectively referred to as "drugs" or "agents").

Cancer may be diagnosed by a number of methods and procedures including radiographic scanning of the suspected tissue or organ. One such method includes the gamma scan of an injected dose of a radioactive material such as technetium 99m as discussed in detail below.

The common goal of cancer treatments has been to eliminate or ameliorate cancerous tumors/cells, with minimal toxicity to the normal cells/tissue and without unpleasant or sometimes life-threatening side effects.

The delivery of an anticancer drug or agent may be accomplished in numerous ways, such as by irradiation, injection, etc. The intraarterial infusion of anticancer drugs is a widely used procedure which has been used to produce an increase in local tumor effect while attempting to reduce systemic drug toxicity. In this method of treatment, cytotoxicity within the tumor is dependent on drug concentration and the duration of exposure of the tumor to the drug. Drug concentration within the tumor depends upon the amount of blood flow to the tumor, the intra-tumoral deposition of the drug and the required metabolic uptake of the chemotherapeutic agent. The duration of exposure of the drug to the cancerous tumor relates to the rates of blood flow and drug uptake and elimination. E. Kim, *Journal of Nuclear Medicines*, Vol. 24, No. 10, p. 966.

Conventional methods of intraarterially providing an anticancer drug by injecting the dosage into an artery supplying the organ suspected of having a neoplasm, result in the drug or agent being quickly removed from the cancerous site due to the circulation of blood and fluids through that organ. T. Kato, et al., *Journal of the American Medical Association*, Vol. 245, No. 11, p. 1123–1127 (March 1981).

One such conventional cancer therapy utilizes an intraperitoneal or intracavitary injection of a colloidal suspension of the radioactive isotope phosphorous 32, i.e., $^{32}P$, which is commercially available from Mallinckrodt Medical, Inc., St. Louis, Mo. 63134, and sold under the trademark PHOSPHOCOL P 32. PHOSPHOCOL P 32 is a chromic phosphate $^{32}P$ suspension with a concentration of up to 185 megabecquerels (5 millicuries) per milliliter and a specific activity of up to 185 megabecquerels (5 millicuries) per milliliter at the time of standardization. PHOSPHOCOL P 32 is supplied as a sterile, nonpyrogenic aqueous solution in a 30% dextrose solution with 2% benzyl alcohol added as a preservative. Each milliliter contains 1 mg sodium acetate. Sodium hydroxide or hydrochloric acid may be present for Ph adjustment.

Phosphorus-32 decays by beta emission with a physical half-life of 14.3 days. The mean energy of the beta particle is 695 keV. D. Kocher, *Radioactive Decay Data Tables*, DOE/TIC 11026, page 70 (1981). The presence of the radioactive phosphorous in a tumor bearing region is determined by using beta scanning equipment modified to scan "bremsstrahlung" radiation. Since a portion of the injected radioactive phosphorous preferentially binds to the tumor, a radiation scan modified to record filtered "bremsstrahlung" will produce an image of the tumor, while a gamma scan with Technetium 99 will produce an image of non-tumor tissue as discussed below.

Unfortunately, a method of effectively administering the therapeutically effective colloidal phosphorous isotope suspension (and other isotopes) so that the isotope remains in contact with the cancerous tissue (e.g., in solid tumors) for the desired time period in internal organs, has eluded researchers and physicians alike for many years. The amount of time therefore that tumors in internal organs are exposed to the isotope or therapeutic drug or other agent is often less than desirable, since the drug is removed relatively quickly from the cancerous site (i.e., "washed out" or "cleared") into the rest of the body through the circulation. The wash out effect also results in the isotope or drug infiltrating non-cancerous tissue/cells, potentially damaging or destroying those structures. With this complicating limitation, radioactive drugs or agents, as well as some drugs, have not been administered and/or are not successful in achieving desirable results in the treatment by arterial or venous infusion of cancers of internal organs and internal sites.

One attempt to solve this problem utilized a colloidal chromic phosphate ($P^{32}$) solution injected into the hepatic artery and portal vein of dogs and man. B. Levine, et al., *Cancer*, Vol. 10, p. 164–171 (1957). However, the researchers concluded that radioactive colloidal chromic phosphate could not be deposited within intrahepatic malignant tumor tissue, and that almost all of the radioactivity present was present in normal liver tissue. This was due to recirculation of the isotope after failing to remain within the tumor.

The present invention is therefore addressed to partially or totally diminishing the exiting vascular flow of a tumor bearing region to permit an intraarterially supplied agent to remain in contact with the tumor or tumor bearing region and not be immediately eliminated or "washed out" from that region. The present invention accomplishes this goal by the use of macro aggregated proteins such as albumin.

Many prior art methods attempting to achieve the goal of effective and targeted drug delivery have been met with very limited success. One method tried intra-arterially infused chemotherapeutic agents in combination with an arterial occlusion to prolong the transit time of the drug through the tumor's vascular bed. The investigators carrying out this method believed that the occlusion prolonged the transit time of the drug through the tumor's vascular bed, thereby increasing the contact time of the drug with the tumor cells. E. Kim, *Journal of Nuclear Medicine,* Vol. 24, No. 10, p. 966. In these attempts to produce an occlusion, the investigators tried to use a variety of materials such as polyvinyl alcohol, foam particles, gelatin sponge fragments, and stainless steel coils implanted into the patient. In order to visualize or measure the rate of occlusion, the investigators also used the conventional imaging procedure which uses a solution of technetium Tc 99m macro aggregated protein to view the sites by examining the amount of gamma radiation given off by the technetium. However, many of the articles used in that study to produce an occlusion had to be surgically implanted and were therefore less than desirable. In addition, the vasculature of the tumor has not always been accessible.

Prior to the present invention, there has therefore been a long felt need for a simple, easy and fast method of preventing the rapid clearance of therapeutic agents, such as isotopes, radioimmunoconjugates and anticancer drugs, from the desired sites.

The use of technetium 99m macroaggregated albumin solely as an imaging agent is well known in the art. A. Bledin et al., *The British Journal of Radiology,* Vol. 57, No. 675, p. 197-203 (March 1984); H. Jacobson, et al., *Journal of American Medical Association,* Topics in Radiology/Nuclear Radiology, Vol. 250, No. 7, p. 941-943 (August 1983); C. Tula, et al., *Clinical Nuclear Medicine,* Vol. 8, p. 131-132 (March 1983).

Technetium Tc 99m decays by isomeric transition with a physical half-life of 6.02 hours. The principal photon that is useful for detection and imaging studies in gamma-2, having a mean%/disintegration of 89.07 and a mean energy level of 140.5 keV.

One prior art technetium imaging kit which is commercially available is the "MPI MAA Kit, Kit for the Preparation of Technetium Tc 99m Albumin Aggregated Injection" which includes radioactive technetium Tc 99m and albumin aggregated protein. This kit is sold as Product No. 44322, by MEDI+PHYSICS, INC., of Arlington Hts., Ill. 60004, and is manufactured by Merck Frosst Canada, Inc. of Kirkland, Quebec, Canada. The product literature accompanying the kit indicates that the kit contains 10 multidose reaction vials which contain the sterile, non-pyrogenic, non-radioactive ingredients necessary to produce technetium Tc 99m albumin aggregated injection for diagnostic use by intravenous injection. Each 10 ml reaction vial contains 2.5 mg of albumin aggregated, 5.0 of albumin human, 0.06 mg (minimum) stannous chloride (maximum stannous and stannic chloride 0.11 mg) and 1.2 mg of sodium chloride. The contents are in a lyophilized form under an atmosphere of nitrogen. Sodium hydroxide or hydrochloric acid is used for pH adjustment. No bacteriostatic preservative is present.

The aggregated particles are formed by denaturation of human albumin in a heating and aggregation process. Each vial contains approximately 4 to 8 million suspended particles. The kit indicates that the average number of particles in a vial is 6 million. By light microscopy, more than 90% of the particles are between 10 and 70 micrometers, while the typical average size is 20 to 40 micrometers; none is greater than 150 micrometers. The Technetium Tc 99m Albumin Aggregated Injection for intravenous use is in its final dosage form when sterile isotonic sodium pertechnetate solution is added to each vial. No less than 90% of the pertechnetate Tc 99m added to a reaction vial is bound to aggregate at preparation time and remains bound throughout the 6 hour lifetime of the preparation.

$^{99}$Technetium is used for three major purposes of scanning. As $^{99}$Technetium colloid, it is a liver scanning agent demonstrating the presence of tumor by the absence of isotopic uptake. $^{99}$Technetium also is used to scan for bony metastasis giving a positive isotopic image. $^{99}$Technetium macroaggregated albumin is used for scanning pulmonary emboli (blood clots) by the absence of the isotope.

Prior to the present invention, there has therefore been a long felt need for a simple, easy and fast method of preventing the rapid clearance of therapeutic agents, such as isotopes, radioimmunoconjugates and anticancer drugs, from the desired sites.

Prior to the present invention, therapeutic agents such as monoclonal antibodies, radiopharmaceuticals and radioactive growth factors were limited in efficacy due to the inability to deposit significant quantities of the agents in cancer, e.g., solid tumor cancers. Carrasquillo, J. A., Radioimmunoscintigraphy with polyclonal or monoclonal antibodies, Zalutsky M (ed.), Antibodies in Radiodiagnosis and Therapy, Boca Raton, Fla., CRC Press, pages 169–198 (1988).

The present invention describes a new technique which, by direct infusion of a blocking material followed by cytotoxic agents into the interstitium, increases tumor deposition of these agents, both experimentally and in clinical application. The clinical technique causes no acute symptoms may be carried out on an out-patient basis, and will allow for a host of new agents to be evaluated for therapeutic efficacy due to the greater tumor concentrations achieved (84–94%) of the infused dose.

Three major physiological factors in cancer have been identified which inhibit significant tumor concentrations of cytotoxic agents. They include elevated interstitial pressure, a large transport distance in the interstitial space of tumors and the tumor's heterogeneous vascular supply. Delivery of novel therapeutic agents in tumors: physiological barriers and strategies, J. National Cancer Institute, Jain, R. K., Vol. 81, pages 570–576 (1989). In addition, the persistence time required for the interaction of cytotoxic agents and the tumor cannot be easily achieved J. National Cancer Institute, Jain, R. K., Vol. 81, pages 570–576 (1989), (see FIGS. 1 and 2). Following intravenous infusion, the circulation causes volumetric dilution and reduces persistence time. This is further complicated by continued recirculation of the agents throughout the body, thus further reducing the opportunity for binding in the tumor.

Accordingly, a need exists for a use of particles such as macro aggregated proteins or peptides in the effective treatment of a variety of diseases and conditions to increase the retention time of the therapeutic agent at a desired treatment site. In addition, a need exists to deliver a therapeutic agent to an organ or other body portion which may not be completely accessible to the vascular injection of the therapeutic agent due, perhaps in part, to tumor growth.

OBJECTS OF THE INVENTION

Accordingly, it is a general object of this invention to provide a method and compositions for delivering cytotoxic agents to cancers, including solid tumor cancers.

It is a further object of this invention to provide a use of aggregated proteins to partially or totally diminish the vascular flow to a tumor or tumor bearing region to permit a therapeutically active agent to remain adjacent and/or in contact with the tumor or tumor bearing region for an extended time period.

It is yet still another object of this invention to provide a method of partially or totally diminishing the vascular flow to a tumor or tumor bearing region which can be accomplished without the need for surgery.

It is yet another object of this invention to provide a method of decreasing the wash out effect of a therapeutically active agent from a targeted site due to the circulation of bodily fluids in the vicinity of or through the targeted site.

It is another object of this invention to provide a method of treating solid tumor cancers by injecting macro aggregated proteins and colloidal radioactive phosphorous.

SUMMARY OF THE INVENTION

These and other objects of this invention are achieved by a method of treating solid tumor cancer in a living being by prolonging the time a therapeutically effective agent remains in the tumor. The method comprises the steps of selecting particles of an aggregated protein and injecting them interstitially into the tumor. The therapeutically effective agent selected from the group consisting of colloidal radioactive phosphorous is injected into the tumor either after the injection of the proteinaceous particles, or simultaneously.

DETAILED DESCRIPTION OF THE PREFERRED EMBODIMENTS

The present invention relates to a new and useful method in the treatment of cancer and other diseases where it is desirable to retain a therapeutically effective agent in or about a targeted site in the body, e.g., a tumor bearing region, for a predetermined time period, without the body "washing out" or clearing the agent from that site, immediately or soon after administration thereof.

Typically, cancerous tumors may be treated by a variety of methods and treatments including drug or immunotherapy. These therapies rely upon delivery to the tumor of a dose of the therapeutic agent, be it a radioactive isotope, such as the conventionally used $^{32}P$, a radioactive antibody, a cytotoxic chemical, a lymphocyte, a macrophage, etc.

The present invention in a first embodiment achieves the long sought after method of partially or totally diminishing the vascular supply to a region such as a tumor bearing region to permit a therapeutic agent to remain in contact with, adhere to, be located in or about the tumor, and thereby have the desired effect. The present invention achieves this goal by utilizing an aggregated protein. More specifically, macro aggregated proteins such as albumin, gamma globulin, or any other suitable protein or peptides or combinations thereof are suitable for use with the present invention.

In accordance with the present invention, the protein may be macro aggregated by conventional methods and available from commercial sources. A preferred source of the macro aggregated protein suspended in a relatively inert carrier fluid is the previously described MPI MAA KIT from MEDI+PHYSICS, INC., although it should be realized to those skilled in the art that any suitable source of protein or other similar acting material may be utilized.

An alternative and most preferred source of the aggregated protein is commercially available product sold under the trademark TechneScan ® MAA, Kit for the Preparation of Technetium Tc 99m Albumin Aggregated, sold by Mallinckrodt Medical Inc., St. Louis, Mo., 63134. The product literature for this kit states that the kit contains 10 milliliter multidose reaction vials containing 2 milligrams of aggregated albumin human, 0.5 milligram of albumin human, and other ingredients such as stannous chloride, lactose, succinic acid and sodium acetate, in lyophilized form under an atmosphere of nitrogen. The product literature states that each vial contains approximately $8 \pm 4 \times 10^6$ aggregated albumin particles and that the particle size distribution of the aggregated albumin is such that not less than 90 percent are 10 to 90 microns in size, typically, approximately 90 percent are within the 10 to 70 micron range.

The desired number of suspended protein particles, upon suspension in an inert fluid, may be easily transferred to a conventional syringe or other delivery instrument, since the particles are normally held or suspended in a solution in utilizing the kits described above, as set forth in the accompanying product literature, prior to the transfer of any of the suspended protein particles, it is preferable to ensure that the particles have not agglomerated and are suspended relatively uniformly throughout by gently inverting the container holding the suspended particles. In using the products discussed above, the formation of foam should be avoided, which sometimes arises in solutions containing proteins.

It is necessary to obtain the desired number of protein particles to be injected into the vascular system and/or tumor of the patient. While the number of particles which may be injected or otherwise delivered will vary depending upon the patient's blood pressure, blood flow rate, metabolism, body weight, organ weight, etc., it has been found that approximately 600,000 to 2,500,000 or more particles of a macro aggregated protein should be suspended in an biologically safe solution and delivered to the patient, although larger quantities of particles may be necessary and desirable depending on various circumstances and conditions of use, e.g., tumor size, etc. In the preferred embodiment, these protein particles are approximately 10–150 micrometers in size, and more preferably in the range of 10–70 micrometers, and perhaps even 20–40 micrometers. By knowing the concentration of particles in a given volume of solution, as with the MEDI+PHYSICS product, one merely needs to withdraw and inject the desired volume of liquid containing the desired number of particles.

In a first embodiment of the method of the present invention, these particles are then provided into the vascular system which feeds or supplies the targeted site, e.g., the tumor bearing region. In a first preferred embodiment, the particles are injected intraarterially into the vascular supply system of the tumor bearing region, e.g., the artery supplying the tumor or tumor bearing region in the liver or other organ or site desired to be treated.

Thereafter, the therapeutically effective agent may be similarly introduced. This therapeutically effective agent can be almost any effective agent which is effective to treat the disease or disorder from which the patient is suffering. A typical example would be cancers, such as solid tumor cancers, however it should be readily apparent to those skilled in the art that the present invention should not be limited only to cancer treatment.

One type of therapeutic agent which is effectively delivered via the present invention is the previously described colloidal radioactive phosphorous ($^{32}P$). Although colloidal radioactive phosphorous has been utilized in the intraperitoneal and intrapleural treatment of cancer for many years, prior to the present invention, its effectiveness has been limited and has not been satisfactorily applied intraarterially. This lack of effectiveness in the intraarterial route is due to the fact that the injected colloidal radioactive phosphorous is rapidly removed from the targeted site and is circulated throughout the body residing in the reticuloendothelial tissue of the normal spleen or liver. The rapid clearance time not only decreases the time the colloidal radioactive phosphorous has to bind to and/or destroy the cancerous tissue, but also undesirably contaminates other body areas. It has been discovered that it is preferable that the colloidal radioactive phosphorous remain in contact with the cancerous tissue for approximately 15 minutes, to permit the phosphorous to bind or adhere to the cancerous tissue, to obtain the desired therapeutic effect. The present invention achieves this goal.

In the present invention, after injection of the suitable number of particles in accordance with the invention, 95% to 98% of the injected dose adheres to the tumor, significantly increasing the effectiveness of the radioactive component.

In a second embodiment of the present invention, the foregoing quantities and types of materials may be directly injected e.g., interstitially, into the tumor itself or other desired sites in accordance with the previously described sequence of steps. For example, solid tumors may be located by conventional techniques such as CAT scanning, to obtain their location. Thereafter the foregoing quantities and types of materials may be introduced, e.g., injected directly into the tumor, such as a solid tumor.

The second method of the present invention is the most preferred embodiment of the present invention and has great significance for many individuals whose vascular supply to a particular organ may be compromised due to tumor growth and blockage. For example, three out of five patients having pancreatic cancer may suffer from a compromised vascular supply to the pancreas. This type of blockage may affect the ability of a therapeutic agent supplied through the vascular system to access the tumor site. This deficiency is overcome by the second method of the present invention.

The second method of the present invention also further reduces the amount of therapeutic agent which is washed out into the surrounding organs or tissues, since the various components are not directly injected into a vascular supply. The second embodiment also is effective in delivering a specified quantity of the therapeutic agent to the desired situs since the materials are not introduced into a vascular supply but directly into the tumor, e.g., solid tumor, or other situs. By injecting a radioactive therapeutic agent directly into a tumor, versus into the vascular supply of the tumor bearing region, there is a ten-fold decrease in the amount of radioactive therapeutic agent which is incorporated into the blood of the patient. For example, a typical intravascular injection as set forth above, may result in a wash out effect of approximately 100–200 nanocuries per milliliter of blood, a marked decrease over the prior art methods. A typical interstitial injection will result in a wash out effect of only 10 to 20 nanocuries per milliliter of blood, an even greater accomplishment over the prior art than the intravascular delivery method.

The process can be repeated as often as allowable and desirable depending upon acceptable blood counts and desired dose of the active therapeutic ingredient to be achieved. In subsequent repetitions of the method of the present invention, it has been found that subsequently larger amounts of the macro aggregated albumin may be desired. For example, if the therapeutic agent is first injected with approximately 1,200,000 particles, a second treatment, perhaps days or weeks later, in accordance with the present invention may be approximately 2,500,000 or more particles. In addition, if the first treatment utilizes 2,000,000 particles, a suitable subsequent treatment may utilize approximately 3,000,000. These dosages may also vary depending upon the size of the tumor, larger tumors requiring larger amounts of macro aggregated albumin or other suitable particles.

In the most preferred embodiment of the second method of the present invention, the suspended protein particles are first injected into the targeted site, e.g., tumor. Next, the therapeutic agent is then delivered to the targeted site. In an alternative embodiment, the second injection may include a quantity of suspended protein particles as heretofore described.

This technique of interstitial blockade and infusion under CT guidance is easily reproduced and, in an era of novel therapeutic agents and medical cost efficiency (no hospitalization), may now be explored both in preclinical experimental programs and, when warranted, in clinical cancer.

Any suitable aggregated protein may be utilized in the present invention, including albumin, gamma globulin, peptides and combinations thereof.

Without further elaboration the foregoing will so fully illustrate my invention that others may, by applying current or future knowledge, adapt the same for use under various conditions of service.

I claim:
1. A method of treating solid tumor cancer in a living being, the method comprising the steps of:
   (a) selecting particles of macroaggregated albumin having an approximate diameter of 10 to 150 micrometers and wherein not less than 90 percent of the particles are approximately 10 to 90 microns in size;
   (b) injecting at least 2,000,000 of the particles into the tumor; and
   (c) then injecting colloidal radioactive chromic phosphate $^{32}P$ into the tumor.
2. The method of claim 1 additionally comprising selecting the number of particles to be injected into the tumor to be at least 2,500,000.
3. A method of treating solid tumor cancer in a living being by enabling colloidal radioactive chromic phosphate $^{32}P$ to remain in contact with the cancerous tissue to permit colloidal radioactive chromic phosphate $^{32}P$ to be taken up by the cancer, the method comprising the steps of:
(a) selecting particles of macroaggregated albumin having an approximate diameter of 10 to 150 micrometers and wherein not less than 90 percent of the particles are approximately 10 to 90 microns in size;
(b) injecting at least 2,000,000 particles of the albumin into the tumor; and
(c) injecting colloidal radioactive chromic phosphate $^{32}P$ into the tumor.

* * * * *